United States Patent
Bacchetta et al.

(10) Patent No.: US 6,309,101 B1
(45) Date of Patent: Oct. 30, 2001

(54) INTRAORAL DENTAL RADIOGRAPHIC FILM PACKET WITH FORMED COMFORT ENHANCING PERIMETER

(75) Inventors: Richard W. Bacchetta; Scott H. Schwallie, both of Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/534,372

(22) Filed: Mar. 24, 2000

(51) Int. Cl.⁷ ........................................... A61B 6/14
(52) U.S. Cl. ............................. 378/169; 378/168
(58) Field of Search ...................... 378/168, 169

(56) References Cited

U.S. PATENT DOCUMENTS

| | | |
|---|---|---|
| 1,537,925 | 5/1925 | Bolin . |
| 1,631,497 | 6/1927 | Marler . |
| 2,084,092 | 6/1937 | Kenney . |
| 4,108,308 * | 8/1978 | Franke et al. . |
| 4,626,216 | 12/1986 | Strong-Grainger . |
| 4,791,657 * | 12/1988 | Kirsch et al. ..................... 378/169 |
| 4,805,201 | 2/1989 | Strong-Grainger . |
| 4,847,884 | 7/1989 | Dove . |
| 4,852,143 * | 7/1989 | Scheier et al. ..................... 378/168 |
| 4,911,871 | 3/1990 | Liese, Jr. . |
| 4,912,740 * | 3/1990 | Liese, Jr. ........................... 378/169 |
| 4,913,288 | 4/1990 | Tanaka . |
| 4,922,511 * | 5/1990 | Gay ................................... 378/169 |
| 5,044,008 * | 8/1991 | Jackson ............................. 378/168 |
| 5,077,779 * | 12/1991 | Steinhausen, Jr. ................ 378/168 |
| 5,170,423 * | 12/1992 | Yurosko ............................ 378/168 |
| 5,285,491 | 2/1994 | Muylle et al. . |
| 5,395,681 * | 3/1995 | Hargarter et al. . |
| 5,784,433 | 7/1998 | Higa . |

* cited by examiner

Primary Examiner—Robert H. Kim
Assistant Examiner—Pamela R. Hobden
(74) Attorney, Agent, or Firm—Mark G. Bocchetti

(57) ABSTRACT

An intraoral x-ray film packet is taught which includes a perimetric comfort enhancing feature. The intraoral x-ray film packet includes an envelope formed by a first outer sheet having a first generally semicylindrical perimetric element formed therein; a second outer sheet including a second generally semicylindrical perimetric element formed therein, the first and second generally semicylindrical perimetric elements forming a perimetric cushion; and a pair of continuous perimetric seals affixing the first and second outer sheets together, one perimetric seal residing on each side of the perimetric cushion. The packet also includes a film chip residing between the first and second outer sheets. The second outer sheet includes a pair of overlapping sections which are sealed together to form a tab portion to facilitate removal of the envelope after exposure.

15 Claims, 2 Drawing Sheets

INTRAORAL DENTAL RADIOGRAPHIC FILM PACKET WITH FORMED COMFORT ENHANCING PERIMETER

FIELD OF THE INVENTION

The present invention relates generally to x-ray film packets and, in particular, to intraoral radiographic film packets with comfort enhancing features.

BACKGROUND OF THE INVENTION

A common problem experienced by people visiting the dentist is the discomfort and pain associated with the taking of dental x-rays caused by the positioning of intraoral radiographic film packets in the patient's mouth. The typical intraoral rear graphic film packet includes relatively hard and/or sharp edges which press against and irritate the gums and other oral soft tissue of the person whose teeth are being x-rayed. A variety of intraoral x-ray dental packets are known in the prior art which include features intended to be comfort enhancing. In addition, attempts have been made to create comfort enhancing structures into which intra-x-ray dental packets can be inserted prior to placement in the patient's mouth. One example of this type of structure is taught in U.S. Pat. No. 5,044,008 titled "Dental Film Cartridge Cushion," by Reginald B. Jackson, Aug. 27, 1991. Jackson utilizes a cartridge cushion comprising a foam sheet sandwich into which the x-ray dental packet is placed for the purpose of cushioning and increasing the comfort to the patient. Jackson requires the manual insertion of the x-ray packet into the cartridge cushion. Thus, Jackson adds significant bulk to the packet and enhances the possibility of triggering a gag reflex action in the patient. Additionally, after the cartridge cushion is removed from the packet, it would be possible to reuse the cartridge cushion which would not be sanitary.

A second example of an add-on structure is taught in U.S. Pat. No. 5,285,491 titled "Dental Film Packet," by Wilfried Muylle et al., Feb. 8, 1994. Muylle et al. teaches sealing a film pack in an envelope consisting of a pair of thin pockets of injection molded plastic which are sealed with a band of adhesive tape. The envelope has no sharp edges and generally rounded corners. Thus, as with Jackson's device, this device requires manual insertion of the packet, adds significant bulk to the packet, enhances the possibility of triggering a gag reflex in the patient, and can also be reused in a non-sanitary manner.

U.S. Pat. No. 1,631,497 titled "Dental X-ray Film Package," by Harry L. Marler, Jun. 7, 1927, teaches a dental x-ray film package wherein a sensitized sheet is sandwiched between two opaque sheets. A heavy band of rubber is stretched about the periphery of the package to hold the package securely together and to provide the light-tight joint.

U.S. Pat. No. 1,537,925 titled "Dental X-ray Film Package," by Leonard M. Bolin, May 12, 1925, teaches a dental x-ray film package wherein a pair of film sheets and the cover sheet are inserted into the container. The container consists of a frame including a backing portion in an enlarged continuous beading about the periphery thereof. The beading must be forced away from the backing portion and stretched peripherally in order to insert the film sheets and cover sheet therein. The container thus serves to hold the package together and provide the light seal.

U.S. Pat. No. 4,791,657 titled "Intraoral Radiographic Film Packet," by Alan Kirsch et al., Dec. 13, 1988, teaches a dental radiographic film packet which includes soft corners for greater patient comfort. The packet is constructed by removing all material from the corners of a typical dental radiographic film packet with the exception of the film chip. Individual corner covers which are seamless pockets are then added to the four corners of the packet. The corner covers create an airspace at each corner around the edge of the film chip.

U.S. Pat. No. 2,084,092 titled "Intraoral Radiographic Film Packet," by Alan Kirsch et al., Dec. 13, 1988, teaches a dental film holder that is a stretchable vellum rubber plate with integral corner pockets into which an x-ray dental packet may be manually inserted. Kenney's dental film holder is intended to be reusable.

From the foregoing it can be seen that many attempts to add a comfort enhancing feature to dental x-ray film packets have resulted in structures requiring manual assembly and/or modification of individual film packets in order to receive comfort enhancing structure. Further, such prior art attempts have failed to provide a dental x-ray film packet in which the comfort enhancing feature is formed integrally therewith during manufacture and without requiring manual assembly.

SUMMARY OF THE INVENTION

It is therefore an object of the present invention to provide an intraoral radiographic film packet with a comfort enhancing perimeter.

It is a further object of the present invention to provide an intraoral radiographic film packet which has a comfort enhancing perimeter integrally formed therewith.

Yet another object of the present invention is to provide an intraoral radiographic film packet including a comfort enhancing perimeter which does not significantly increase the bulk of the film packet.

Still another object of the present invention is to provide a comfort enhancing perimeter feature for an intraoral radiographic film packet which cannot be reused in a non-sanitary manner.

The foregoing and numerous other features, objects and advantages of the present invention will become readily apparent upon a review of the detailed description, claims and drawings set forth herein. These features, objects and advantages are accomplished by forming each of the two outer thermoplastic layers of the x-ray packet with a perimetric hollow semicylindrical feature. Sandwiched between these two outer thermoplastic layers are the typical elements comprising a dental film pack including a paper wrap, the film chip and a lead shield. With these typical elements sandwiched between the two outer thermoplastic layers, the two outer thermoplastic layers are sealed to one another both inside and outside the perimetric cylinder formed by the interface of the two perimetric semicylindrical features. Sealing can be accomplished by heat sealing, RF sealing, or any other type of sealing which would yield a substantially airtight perimetric cylindrical chamber. In such manner, the dental film packet is created which includes an integrally formed perimetric cushion.

DETAILED DESCRIPTION OF THE INVENTION

Figure 1:
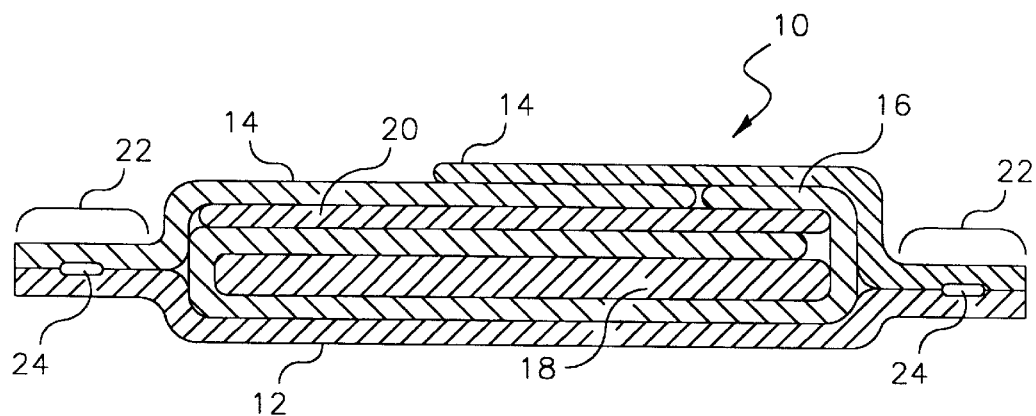
FIG. 1 is a cross-sectional view of a typical prior dental film packet.

Turning first to FIG. 1, there is shown a cross-section of a typical prior art dental film packet 10. Dental film packet 10 includes an outer envelope comprising a vinyl sheet 12 on one face of the dental film packet 10 and a pair of overlapping vinyl sheets 14 on the opposite face thereof. Contained between the sheet 12 and overlapping sheets 14 are a paper wrap element 16, a film chip 18 and a lead foil 20. Vinyl sheets 12 and 14 project beyond dimensions of the paper wrap element 16, the film chip 18 and lead foil 20 to yield a perimetric edge 22. Laminated perimetric edge 22 allows for heat sealing of vinyl sheets 12 and 14 to one another to yield a light tight perimeter to the dental film packet 10. In addition, a heat seal 24 is generated at the overlap of vinyl sheets 14 to provide an outer envelope which is completely light-tight and which is substantially watertight. This prior art dental film packet 10 therefore includes a laminated, relatively stiff and sharp perimetric edge created by the laminated perimetric edge 22. It is this relatively stiff and sharp perimetric edge which causes discomfort to the patient.

Figure 2:
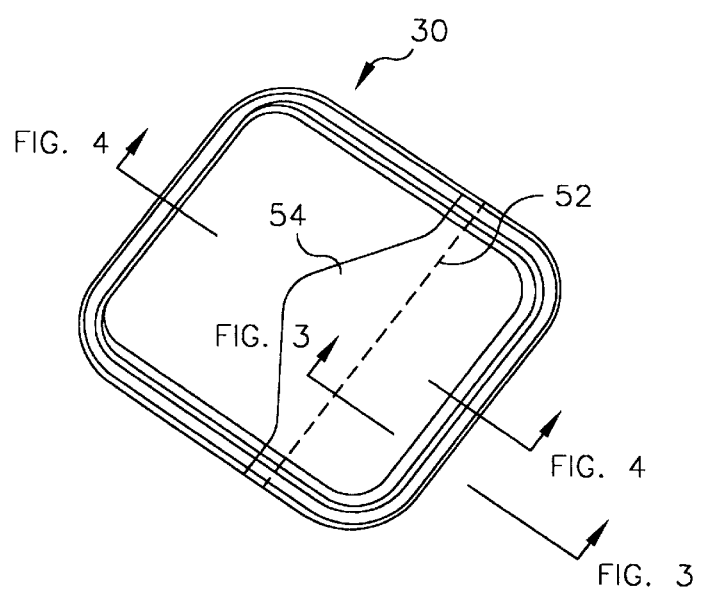
FIG. 2 is a perspective view of the intraoral radiographic film packet with comfort enhancing features of the present invention.
Figure 3:
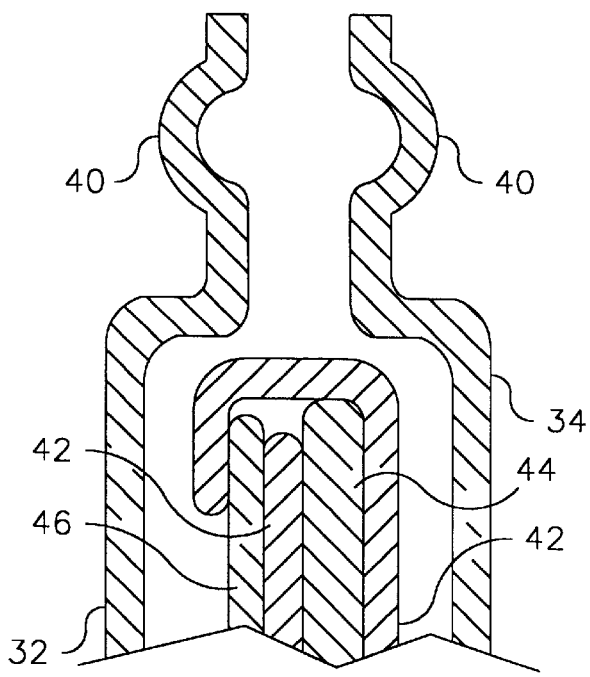
FIG. 3 is a partially exploded cross-sectional view of the intraoral radiographic film packet of the present invention taken along line 3—3 of FIG. 2.
Figure 4:
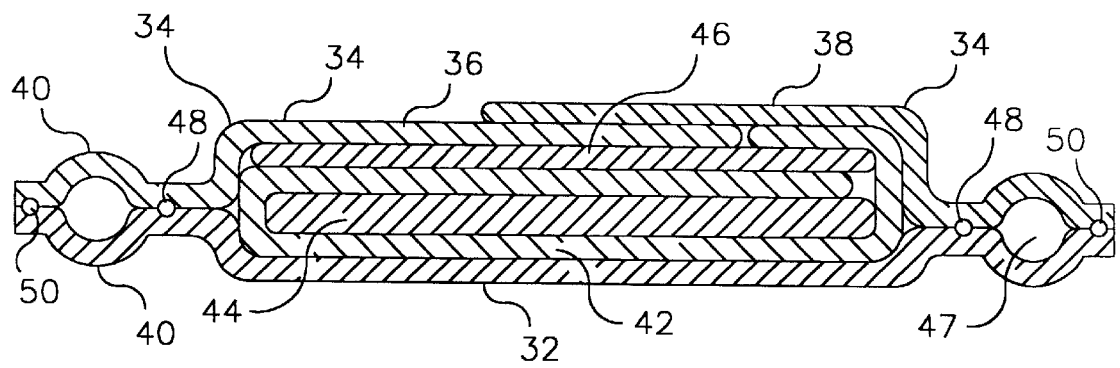
FIG. 4 is a partial cross-sectional view of the intraoral radiographic film packet of the present invention taken along line 4—4 of FIG. 2.

Turning next to FIGS. 2, 3 and 4, there is shown the dental film packet 30 of the present invention. Dental film packet 30 includes an envelope comprising a first outer sheet 32 and an opposing second outer sheet 34. Second outer sheet 34 is actually comprised of a pair of overlapping sections 36 and 38. Each outer sheet 32 and 34 includes a perimetric generally semicylindrical element 40 formed therein. The forming of outer sheets 32 and 34 can be by a variety of techniques including vacuum forming, molding, embossing, or the like. Outer sheets 32 and 34 are preferably made of a soft thermoplastic material such as, but not limited to polyvinyl chloride (PVC), or ethylene vinyl acetate (EVA). Sandwiched between outer sheets 32 and 34 are the typical elements found in a dental x-ray film packet. There is a paper wrap element 42, the film chip 44 and a lead foil 46. The dental x-ray film packet 30 is assembled by placing the paper wrap element 42, the film chip 44 and a lead foil 46 between outer sheets 32 and 34 and sealing the outer sheets 32 and 34 to one another about the perimeter. There are actually two perimetric seals generated (an inner seal and an outer seal, indicated by spots 48 and 50, respectively), one on each side of cylindrical air cushion 47 formed by the interface of the two semicylindrical elements 40. This air cushion 47 provides a comfort edge for the patient. Inner seal 48 and outer seal 50 can be formed by heat sealing, RF sealing, or any other sealing mechanism which can create a substantially airtight bond between outer sheets 32 and 34. There is also a transverse seal (indicated by line 52) affixing overlapping sections 36 and 38 together. Overlapping section 38 is preferably formed with a tab portion 54 which extends past transverse seal 52 to facilitate removal of the envelope for extraction and development of the film chip 44 after exposure.

Those skilled in the art will also recognize that there are now digital radiography products available which are intended to be used in place of dental x-ray film packets. One example of this type of technology uses a plate that is coated with phosphorous. When exposed to radiation, the plate will create an image that can be scanned with a laser into a computer instead of being chemically processed. To the extent that these products have the same problems of patient discomfort, the present invention can be used to solve such problems. Similarly, intraoral products which use a CCD sensor array may also achieve some level of comfort benefit through the application of the present invention.

From the foregoing, it will be seen that this invention is one well adapted to obtain all of the ends and objects hereinabove set forth together with other advantages which are apparent and which are inherent to the apparatus.

It will be understood that certain features and subcombinations are of utility and may be employed with reference to other features and subcombinations. This is contemplated by and is within the scope of the claims.

As many possible embodiments may be made of the invention without departing from the scope thereof, it is to be understood that all matter herein set forth and shown in the accompanying drawings is to be interpreted as illustrative and not in an illuminating sense.

PARTS LIST 10 dental film packet (prior art)
12 outer envelope comprising a vinyl sheet
14 outer envelope comprising overlapping vinyl sheets
16 paper wrap element
18 film chip
20 lead foil
22 laminated perimetric edge
24 heat seal
30 dental film packet (present invention)
32 outer envelope comprising a first outer sheet
34 outer envelope—opposing second outer sheet
36 overlapping sections
38 overlapping sections
40 semicylindrical element
42 paper wrap element
44 film chip
46 lead foil
47 cylindrical air cushion
48 inner seal
50 outer seal
52 transverse seal
54 tab portion

What is claimed is:

1. An intraoral x-ray film packet comprising:

(a) an outer envelope having a perimetric air cushion integrally formed therein; and (b) a film chip contained within said outer envelope.

2. An intraoral x-ray film packet comprising:

(a) a first thermoplastic sheet forming a first face of said x-ray film packet and having a first generally semicylindrical perimetric element formed therein;

(b) a second sheet and a third sheet which overlaps said second sheet, said second and third sheets forming a second face of said x-ray film packet, said second face including a second generally semicylindrical perimetric element formed therein;

(c) a first continuous perimetric seal positioned outside of said first and second generally semicylindrical perimetric elements; and (d) a second continuous perimetric seal positioned inside of said first and second generally semicylindrical perimetric elements, said first and second continuous perimetric seals in combination with said first and second generally semicylindrical perimetric elements yielding a tubular perimetric cushion.

3. An intraoral x-ray film packet comprising:
- (a) a first outer sheet having a first generally semicylindrical perimetric element formed therein;
- (b) a second outer sheet including a second generally semicylindrical perimetric element formed therein, said first and second generally semicylindrical perimetric elements forming a tubular perimetric cushion;
- (c) a film chip residing between said first outer sheet and said second outer sheet;
- (d) a first continuous perimetric seal affixing said first outer sheet and said second outer sheet and positioned outside of said tubular perimetric cushion; and
- (e) a second continuous perimetric seal affixing said first outer sheet and said second outer sheet and positioned between said tubular perimetric cushion and said film chip.

4. An intraoral x-ray film packet as recited in claim 3 wherein:
said second outer sheet comprises a pair of overlapping sections.

5. An intraoral x-ray film packet as recited in claim 4 wherein:
said second outer sheet further comprises a transverse seal affixing said pair of overlapping sections.

6. An intraoral x-ray film packet as recited in claim 5 wherein:
one of said pair of said pair of overlapping sections includes a tab portion to facilitate removal of said first and second outer sheets.

7. An intraoral x-ray film packet as recited in claim 3 wherein:
said first and second outer sheets are made from a thermoplastic material.

8. An intraoral x-ray film packet as recited in claim 3 wherein:
said first and second perimetric seal are formed by RF sealing.

9. An intraoral x-ray film packet as recited in claim 3 wherein:
said first and second perimetric seal are formed by heat sealing.

10. An intraoral x-ray film packet as recited in claim 3 wherein:
said transverse seal is formed by RF sealing.

11. An intraoral x-ray film packet as recited in claim 1 wherein:
said transverse seal is formed by heat sealing.

12. An intraoral x-ray film packet as recited in claim 3 wherein:
said first and second generally semicylindrical perimetric elements are formed by vacuum forming.

13. An intraoral x-ray film packet as recited in claim 3 wherein:
said first and second generally semicylindrical perimetric elements are formed by molding.

14. An intraoral x-ray film packet as recited in claim 3 wherein:
said first and second generally semicylindrical perimetric elements are formed by embossing.

15. An intraoral x-ray film packet as recited in claim 1, said envelope comprising:
- (a) a first thermoplastic sheet forming a first face of said x-ray film packet and having a first generally semicylindrical perimetric element formed therein;
- (b) a second sheet and a third sheet which overlaps said second sheet, said second and third sheets forming a second face of said x-ray film packet, said second face including a second generally semicylindrical perimetric element formed therein;
- (c) a first continuous perimetric seal positioned outside of said first and second generally semicylindrical perimetric elements; and
- (d) a second continuous perimetric seal positioned inside of said first and second generally semicylindrical perimetric elements, said first and second continuous perimetric seals in combination with said first and second generally semicylindrical perimetric elements yielding a perimetric cushion.

* * * * *